United States Patent
Anraku et al.

(10) Patent No.: US 7,090,970 B2
(45) Date of Patent: Aug. 15, 2006

(54) COMPOSITION FOR BLOOD SERUM OR PLASMA SEPARATION AND VESSEL FOR BLOOD EXAMINATION CONTAINING THE SAME

(75) Inventors: Hideo Anraku, Shunan (JP); Ryusuke Okamoto, Shunan (JP)

(73) Assignee: Sekisui Chemical Co., Ltd., Osaka (JP)

( * ) Notice: Subject to any disclaimer, the term of this patent is extended or adjusted under 35 U.S.C. 154(b) by 308 days.

(21) Appl. No.: 10/475,807

(22) PCT Filed: Dec. 3, 2002

(86) PCT No.: PCT/JP02/12623

§ 371 (c)(1),
(2), (4) Date: Oct. 24, 2003

(87) PCT Pub. No.: WO03/048764

PCT Pub. Date: Jun. 12, 2003

(65) Prior Publication Data

US 2004/0129631 A1  Jul. 8, 2004

(30) Foreign Application Priority Data

Dec. 4, 2001 (JP) .............................. 2001-370336

(51) Int. Cl.
*A01N 1/02* (2006.01)
*C09K 3/00* (2006.01)
*G01N 33/48* (2006.01)
*B01D 21/26* (2006.01)

(52) U.S. Cl. .............................. 435/2; 210/516; 252/60

(58) Field of Classification Search ............. 210/500.1, 210/513, 516, 518; 435/2; 436/8; 252/60; 585/16, 18, 20, 21, 23, 24, 25, 26; 422/102
See application file for complete search history.

(56) References Cited

U.S. PATENT DOCUMENTS 5,510,237 A * 4/1996 Isogawa et al. ................. 435/2
5,776,357 A * 7/1998 Okamoto et al. ............. 252/60

FOREIGN PATENT DOCUMENTS

| JP | 51-83654 |   | 7/1976 |
| JP | 53-042283 |  | 4/1978 |
| JP | 55-043462 |  | 3/1980 |
| JP | 58-035463 |  | 3/1983 |
| JP | 58-137757 |  | 8/1983 |
| JP | 02-95257 | * | 4/1990 |
| JP | 04-337458 |  | 11/1992 |
| JP | 09-501192 |  | 2/1997 |
| JP | 09-124743 |  | 5/1997 |

OTHER PUBLICATIONS

Patent Abstracts of JP 02-095257 (Apr. 1990).*

(Continued)

*Primary Examiner*—John S. Kim
(74) *Attorney, Agent, or Firm*—Townsend & Banta

(57) ABSTRACT

A composition for blood serum or plasma separation which has improved compatibility between a cyclopentadiene oligomer and a phthalic ester and generates no oily ingredient suspending in the blood serum or plasma after centrifugal separation regardless of the conditions for the centrifugal separation; and a vessel for blood examination which contains the composition. The composition for blood serum or plasma separation comprises: a polycyclic hydrocarbon compound having an unsaturated and/or saturated cyclic structure in the molecule and having a solidifying point or pour point of 0° C. or lower; a cyclopentadiene oligomer; and a phthalic ester.

7 Claims, 1 Drawing Sheet

OTHER PUBLICATIONS

JP 6-003356 A, & English Abstract thereof, dated Jan. 11, 1994.
JP 9-015238A, & English Abstract thereof, dated Jan. 17, 1997.
JP 51-83654 A. (No English abstract) Jul. 22, 1976.
JP 55-43462 A & English Abstract thereof, dated Mar. 27, 1980.
JP 9-124743A, & English Abstract thereof, dated May 13, 1997.
JP 53-42283A, & English Abstract thereof, dated Apr. 17, 1978.
JP 4-337458A & English Abstract thereof, dated Nov. 25, 1992.
JP 58-137757A, & English Abstract thereof, dated Aug. 16, 1983.
JP 9-501192A, & English Abstract thereof, dated Feb. 9, 1995.
JP 58-35463A, & English Abstract thereof, dated Mar. 2, 1983.
JP 2-95257A, & English Abstract thereof, dated Apr. 6, 1990.

* cited by examiner

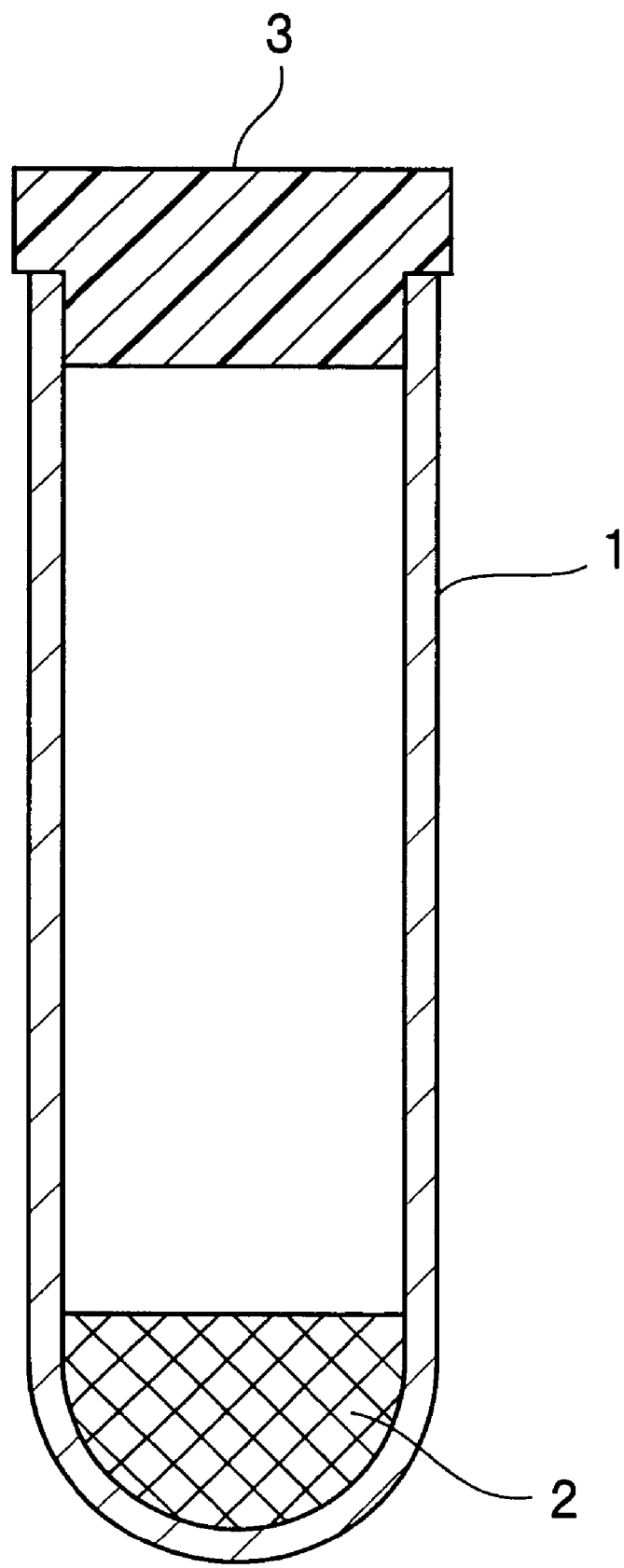

COMPOSITION FOR BLOOD SERUM OR PLASMA SEPARATION AND VESSEL FOR BLOOD EXAMINATION CONTAINING THE SAME

TECHNICAL FIELD

The present invention relates to a composition for use in the separation of blood serum or plasma by utilizing a specific gravity difference between blood components and also to a blood testing container accommodating the composition.

BACKGROUND ART

Japanese Patent Laying-Open No. Sho 51-83654 discloses a blood testing container wherein a thixotropic serum or plasma separator composition, such as a mixture of silicone and silica, has been accommodated at the bottom of a blood collection tube. Blood is collected in the blood collection tube, left to stand for an appropriate period of time and centrifuged. Then, the gel-like serum or plasma separator composition is rendered flowable by the action of a centrifugal force. Also, the gel-like serum or plasma separator composition has a specific gravity (1.03–1.07) intermediate between a serum or plasma component (specific gravity of about 1.02) and a blood clot or cell component (specific gravity of about 1.08). Accordingly, the separator composition gradually rises in the collected blood from the bottom of the tube and positions between the serum or plasma layer and the blood clot or cell layer to define a partition which successfully separates the serum or plasma component from the blood clot or cell component. The serum or plasma component now separated from the blood or cell component can be removed easily from the blood collection tube for submission to various testings. It can also be stored without transferring to another container.

Such a thixotropic serum or plasma separator composition may comprise main components other than those described above. For example, separator compositions have been proposed which, besides the aforementioned silicone, also contains an oligomer and an agent for adjustment of specific gravity, viscosity and/or thixotropic properties. Examples of oligomers include halogenated hydrocarbon oligomers (Japanese Patent Laying-Open Nos. Sho 55-43462 and Hei 09-124743), acrylate ester oligomers (Japanese Patent Laying-Open Nos. Sho 53-42283 and Hei 4-337458), ester oligomers (Japanese Patent Laying-Open No. Sho 58-137757 and Japanese Patent Kohyo No. Hei 9-501192), α olefin-maleate ester oligomers (Japanese Patent Laying-Open No. Sho 58-35463) and cyclic hydrocarbon oligomers (Japanese Patent Laying-Open Nos. Hei 02-95257 and Hei 09-15238). Examples of adjustment agents include inorganic particles such as of silica and kaolin and organic gelation agents such as benzylidene sorbitol.

However, the preceding silicone resins show markedly poor compatibility with the specific gravity and viscosity adjusting agents comprised of the inorganic particles and are highly susceptible to phase separation within a short period of time. Also, the silicone resins undergo a curing reaction when they are subjected to radiation (γ-ray, electron beam or the like) sterilization. Accordingly, the silicone reins are currently little used.

The halogenated hydrocarbon oligomers, when incinerated for disposal, produce halogenated hydrogen gas which possibly gives damage to incinerators or exerts a bad influence upon the environment.

The preceding acrylate ester oligomers, ester oligomers and α olefin-maleate ester oligomers each contains many polar groups in a molecule, which problematically increase the occurrence of drug adsorption when a drug concentration in blood is monitored.

The separator composition containing a phthalate ester and a cyclopentadiene resin as the cyclic hydrocarbon oligomer, as disclosed in Japanese Patent Laying-Open No. Hei 09-15238, is excellent in two respects; drug adsorption is maintained at a low degree of occurrence and generation of toxic incineration gas is avoided. However, the composition contains components which are poorly compatible with each other. On rare occasions, a separated oily component is observed to float in blood serum or plasma after centrifugation.

DISCLOSURE OF THE INVENTION

The present invention is directed toward solving the preceding problems encountered with the prior art and its object is to provide a serum or plasma separator composition which improves compatibility of a cyclopentadiene based oligomer with a phthalic acid ester and avoids the occurrence of an oily component to float in serum or plasma after centrifugation, regardless of the centrifugal conditions selected, as well as providing a blood testing container utilizing the separator composition.

In accordance with a broad aspect of the present invention, a serum or plasma separator composition is provided containing a polycyclic hydrocarbon compound having an unsaturated and/or saturated cyclic structure and a freezing or flow point of 0° C. or below, a cyclopentadiene based oligomer and a phthalic acid ester.

In a particular aspect of the serum or plasma separator composition of the present invention, the unsaturated cyclic structure of the polycyclic hydrocarbon compound is an aromatic ring.

In another particular aspect of the present invention, the serum or plasma separator composition contains from 1 to 300 parts by weight of the polycyclic hydrocarbon compound having an unsaturated and/or saturated cyclic structure and a freezing or flow point of 0° C. or below and from 5 to 40 parts by weight of the phthalic acid ester, based on 100 parts by weight of the cyclopentadiene based oligomer.

In a further particular aspect of the present invention, a blood testing container is provided which accommodates the serum or plasma separator composition according to the present invention.

The present invention is below described in more detail.

Conventionally, there has been a problem that when the serum or plasma separator composition comprised of a phthalate ester and a cyclopentadiene based oligomer is stored for an extended period of time, separation of an oily component from the composition sometimes occurs and this oily component is left to float in the centrifuged serum or plasma.

After energetic studies of the problem, we have found that this separation is attributed to poor compatibility between the phthalate ester, which has intramolecular polar interaction based on ester bonds, and the cyclopentadiene based oligomer which is indeed a nonpolar hydrocarbon.

This finding was followed by further investigation of a possible component which can serves as a compatibilizer of these substances. As a result, we have discovered that the inclusion of the polycyclic hydrocarbon compound having an unsaturated and/or saturated cyclic structure and also having a freezing or flow point of 0° C. or below, as an agent which functions to strengthen hydrophobic interaction, results in the provision of the composition with good compatibility.

Although rare, conventional separator compositions occasionally produce an oily component in the partition-forming stage during centrifugation, which possibly causes clogging of a sampling nozzle in an analyzer or pollution of a reaction cell. However, this discovery has led to successful prevention of such adverse results.

In the present invention, the cyclopentadiene based oligomer (hereinafter may be referred to simply as oligomer) refers to a substance (polymer) formed by increasing a molecular weight of a cyclopentadiene based monomer and may be in the form of a hydrogenated cyclopentadiene-based oligomer (including partially hydrogenated one).

As the oligomer, the preceding cyclopentadiene based oligomer and hydrogenated cyclopentadiene-based oligomer may be use alone or in combination.

The cyclopentadiene based monomer (hereinafter may be referred to simply as monomer) is not particularly specified in type. Examples of such monomers include cyclopentadiene, dicyclopentadiene and alkyl-substituted cyclopentadiene (e.g., methylcyclopentadiene).

The oligomer may be a homopolymer of such a monomer, or alternatively, a copolymer of two or more different monomers. The oligomer may contain an aromatic olefin or other comonomer unit. The oligomer may comprise any combination of such polymers and copolymers.

The oligomer can be made by increasing a molecular weight of the preceding monomer, e.g., via a Diels-Alder reaction. The oligomer is sometimes called a cyclopentadiene-based petroleum resin or a dicyclopentadiene resin (DCPD resin). Preferably, the oligomer is further hydrogenated to saturate the remaining double bonds.

The method used to prepare the cyclopentadiene based oligomer is not particularly specified. Conventional methods can be used including the method disclosed in Japanese Patent Laying-Open No. Hei 9-15238.

A softening point of the oligomer can be determined according to "testing methods for the softening point of hot melt adhesives" specified in JIS K 6863-1994. The softening point of the oligomer is preferably in the range from 70° C. to 140° C., more preferably in the range from 80° C. to 120° C. The softening point, if below 70° C., may increase the occurrence of phase separation of the serum or plasma separator composition, and, if above 140° C., reduces the solubility of the oligomer and sometimes results in the difficulty to prepare the separator composition.

Also, a melt viscosity at 180° C. of the oligomer can be determined according to the A method of "testing methods for melt viscosity of hot-melt adhesives" specified in JIS K 6862-1994. The melt viscosity at 180° C. of the oligomer is preferably in the range from 0.03 Pa·s to 0.5 Pa·s, more preferably in the range from 0.05 Pa·s to 0.15 Pa·s. If the melt viscosity is below 0.03 Pa·s, the viscosity of the present composition may become insufficient. On the other hand, if the melt viscosity exceeds 0.5 Pa·s, the viscosity of the present composition may become excessively high.

A specific gravity at 25° C. of the oligomer (according to the sink-float method using a copper sulfate solution) is preferably in the range from 1.02 to 1.10, more preferably in the range from 1.03 to 1.09. If the specific gravity of the oligomer is either below 1.02 or above 1.10, it may become difficult to suitably adjust the specific gravity of the present composition.

The phthalate ester is not particularly specified in type. Examples of phthalate esters include butylpentyl phthalate, dipentyl phthalate, butylhexyl phthalate, butylheptyl phthalate, dihexyl phthalate, pentylheptyl phthalate, butylnonyl phthalate, pentyloctyl phthalate, xylylhepty phthalate, diheptyl phthalate, heptyloctyl phthalate, dioctyl phthalate, octylnonyl phthalate, diisononyl phthalate, octyldecyl phthalate, diisodecyl phthalate, decylundecyl phthalate, diundecyl phthalate and butylbenzyl phthalate.

If the alcohol residues which respectively forms two ester groups in the phthalate ester have an excessively large carbon number, it becomes difficult to adjust a specific gravity of the present composition within a suitable range. It is thus preferred that each alcohol residue has a carbon number of 11 or below.

The phthalate ester is preferably used in the amount from 5 to 40 parts by weight, more preferably in the range from 7 to 30 parts by weight, based on 100 parts by weight of the cyclopentadiene based oligomer. If the use amount is below 5 parts by weight or exceeds 40 parts by weight, it may become difficult to suitably adjust the viscosity and compatibility of the present composition.

The polycyclic hydrocarbon compound having an unsaturated and/or saturated cyclic structure in a molecule (hereinafter may be referred to as polycyclic compound), as referred to in the present invention, includes at least two cyclic structures in a molecule. The bonding style of rings is not particularly specified. For example, two or more rings may be included separately, as illustrated by biphenyl. Fused rings may be included, as illustrated by naphthalene. A linear hydrocarbon may be included as a substituent.

Also, the polycyclic compound may include O, N, S or other ether linking heteroatom in its molecule.

The unsaturated cyclic structure, as referred to in this invention, means a compound having an unsaturated bond in its cyclic structure, but this compound having an unsaturated bond in its cyclic structure also encompasses aromatic cyclic compounds and aromatic cyclic hydrocarbons (e.g., benzene ring).

Since a freezing point of the phthalate ester is 0° C. or below, a freezing point or flow point of the polycyclic compound also needs to be 0° C. or below. If it exceeds 0° C., the polycyclic compound may show a higher tendency to form agglomerates, rather than forming a uniform blends with the phthalate ester, possibly resulting in the separation thereof from the phthalate ester. Here, the freezing point or flow point of the polycyclic compound is determined according to JIS K 2269.

Preferably, a specific gravity at 25° C. of the polycyclic compound is 0.9 or above. If it is below 0.9, it may become difficult to suitably adjust the specific gravity of the present composition.

Also preferably, a viscosity at 20° C. of the polycyclic compound is 0.1 Pa·s or below. If it exceeds 0.1 Pa·s, it may become difficult to suitably adjust the viscosity of the present composition.

The polycyclic compound including two or more rings in a separate manner, as described above, is not particularly specified. Examples of such polycyclic compounds include alkylbiphenyl (flow point −40° C. or below, specific gravity 0.96, about 0.025 Pa·s), partially hydrogenated triphenyl (flow point −10° C. or below, specific gravity 1.01, about 0.07 Pa·s), dibenzyltoluene (flow point −30° C. or below, specific gravity 1.04, about 0.05 Pa·s), various derivatives and partial hydrides thereof.

In the polycyclic compound having a triphenyl or dibenzyl toluene skeleton, a phenyl or benzyl ring may be attached to an ortho, meta or para position. These may be present in any combination.

The polycyclic compound including fused rings is not particularly specified. Examples of such polycyclic compounds include tetrahydronaphthalene (melting point −30° C. or below, specific gravity 0.98, about 0.002 Pa·s), alkylnaphthalene (flow point −10° C. or below, specific gravity 1.00, about 0.003 Pa·s), various derivatives and partial hydrides thereof.

These polycyclic compounds may be obtained by partial hydrogenation of unsaturated cyclic hydrocarbon compounds, or by chemical bonding of separately-prepared unsaturated and saturated cyclic hydrocarbon compounds.

The serum or plasma separator composition of the present invention preferably contains 1–300 parts by weight of the polycyclic compound and 5–40 parts by weight of the phthalate ester, more preferably 30–100 parts by weight of the polycyclic compound and 7–30 parts by weight of the phthalate ester, based on 100 parts by weight of the cyclopentadiene based oligomer.

If the loading of the polycyclic compound is below 1 part by weight or if the loading of the phthalate ester exceeds 40 parts by weight, compatibility between the cyclopentadiene based oligomer and the phthalate ester may become insufficient. On the other hand, if the loading of the phthalate ester is below 5 parts by weight or if the loading of the polycyclic compound exceeds 300 parts by weight, a relative amount of the polar groups (amount of ester residues of the phthalate ester) present in the composition decreases. As a result, the composition may become less compatible with the inorganic particles or organic gelling agent for use as an adjustor of specific gravity or thixotropic properties. The excessive viscosity reduction of the composition may also result.

Preferably, the viscosity at 50° C. of the composition of the present invention is in the range of 0.1 Pa·s–100 Pa·s, when measured using a rotational viscometer (manufactured by Brookfield Engineering Laboratories, Inc.) at a shear rate of 1 sec$^{-1}$. This not only permits the composition when subjected to a conventional centrifugal operation to position between the serum or plasma layer and the blood clot or cell layer, but also eases an operation for loading the composition into a blood test container such as a vacuum blood collection tube. Also, the viscosity at 25° C. of the composition of the present invention is preferably in the range of 10 Pa·s–500 Pa·s. If its viscosity is excessively low, separation and flotation of an oily component may occur. The excessively high viscosity may result in the occasional difficulty of the composition to position between the serum or plasma layer and the blood clot or cell layer.

The proper specific gravity range of the composition of the present invention may vary depending upon the contemplated application which may require fractionation of a leukocyte component or dilution of a blood specimen, for example. The specific gravity at 25° C. of the composition is preferably in the range from 1.00 to 1.10, more preferably from 1.02 to 1.08. If its specific gravity is excessively low, separation and flotation of an oily component may occur. The excessively high specific gravity may result in the occasional difficulty of the composition to position between the serum or plasma layer and the blood clot or cell layer.

Various additives can also be added to the composition of the present invention for different purposes. Examples of additives are specific gravity or flow adjustors, including fine particles of inorganics such as silica (silicon dioxide), alumina, glass, talc, kaolin, bentonite, titania, zirconia and asbestos; and fine particles (preferably having a mean particle size of 500 μm or below) of organic polymers such as polystyrene, polyurethane and polyacrylate. Other flow adjustors include organic gelling agents. Examples of other additives include anti-degradation agents such as antioxidants and light stabilizers.

Preferred among the listed inorganic fine particles are silica fine particles. Hydrophobic silica fine particles are more preferred which can be obtained via partial substitution of hydroxyl groups on surfaces of silica primary particles by alkyl groups. Further preferred is vapor-deposited amorphous dry silica which exhibits a large specific surface area and can be well dispersed in the present composition.

The dry silica, because of its hydrophobic nature, is well dispersible in the composition comprising the cyclopentadiene based oligomer, phthalate ester and polycyclic compound. Due also to the difficulty of the dry silica to dissolve in blood, the occurrence of hemolysis can be prevented. Accordingly, the occurrence of a blood cell component to be mixed in serum or plasma is prevented and the adverse influence on clinically examined values is reduced. The use of the dry silica is thus preferred.

The silica fine particles preferably have a specific surface area from 10 m$^2$/g to 1,000 m$^2$/g, more preferably from 30 m$^2$/g to 500 m$^2$/g. The specific surface area within the specified range permits suitable adjustment of the thixotropic properties of the present composition.

The silica fine particles preferably have a primary particle diameter from 1 nm to 100 nm, more preferably from 5 nm to 50 nm. The primary particle diameter within the specified range permits suitable adjustment of the thixotropic properties of the present composition.

The silica fine particles are preferably used in the amount from 1 part by weight to 20 parts by weight, more preferably from 2 parts by weight to 10 parts by weight, based on 100 parts by weight of the cyclopentadiene based oligomer. Loading of the silica fine particles within the specified range permits suitable adjustments of the specific gravity and thixotropic properties of the present composition.

Examples of suitable organic gelling agents include condensates of sorbitol and aromatic aldehydes, such as dibenzylidene sorbitol, tribenzylidene sorbitol and alkyl-substituted dibenzylidene sorbitol; and amino acid gelling agents such as N-lauroyl-L-glutamicacid-α, γ-di-n-butylamide. Because of the inability to absorb water and dissolve in water, these gelling agents do not cause the present composition to absorb water and become cloudy even upon extended contact with blood. In addition, they do not cause hemoconcentration or other adverse side effects.

The organic gelling agent is preferably used in the amount from 0.03 parts by weight to 5 parts by weight, more preferably from 0.06 parts by weight to 3 parts by weight, based on 100 parts by weight of the cyclopentadiene based oligomer. Loading of the gelling agent within the above-specified range permits suitable adjustment of thixotropic properties of the present composition. If loading of the gelling agent is excessively low, separation and flotation of an oily component may occur. On the other hand, the excessively high loading thereof may result in the occasional difficulty of the composition to position between the serum or plasma layer and the blood clot or cell layer.

If further necessary, a dispersant for the gelling agent or a solvent may be further added to the composition of the present invention.

The dispersant for the gelling agent preferably has an HLB value from 1.0 to 9.0, more preferably from 4.0 to 6.0. Such a dispersant can be selected from the group consisting of a polyoxyethylene-polyoxypropylene block copolymer, sorbitan fatty acid esters and other nonionic surfactants, and any combinations thereof.

The nonionic surfactant within the above-specified HLB value range improves dispersion properties of the gelling agent and permits suitable adjustments of thixotropic and hydrophobic properties of the present composition. Due to the difficulty of the nonionic surfactant to dissolve in blood, the occurrence of hemolysis can be prevented during the use of the present composition. Also, the occurrence of a blood cell component to be mixed in serum or plasma is prevented. Hence, accurate test results can be obtained.

The nonionic surfactant is preferably used in the amount from 0.1 parts by weight to 15 parts by weight, more preferably from 1 part by weight to 5 parts by weight, based on 100 parts by weight of the cyclopentadiene based oligomer. Loading of the nonionic surfactant within the above-specified range results in the simultaneous improvements of dispersion properties of the organic gelling agent, compatibility of the organic gelling agent with the cyclopentadiene based oligomer and thixotropic properties of the present composition.

The organic gelling agent may be thermally brought into solution or dissolved in a solvent. Examples of useful solvents include 1-methyl-2-pyrrolidone, dimethyl formaldehyde (DMF) and dimethylsulfoxide (DMSO). 1-methyl-2-pyrrolidone is preferably used because of the following reasons: it better dissolves the organic gelling agent; it does not react with blood and thus causes no hemolysis; and it does not decompose when the composition is subjected to radiation sterilization.

The solvent is preferably used in the amount within 5 weight by parts, more preferably within 3 parts by weight, based on 100 parts by weight of the dicyclopentadiene based oligomer. If the use amount exceeds 5 parts by weight, the solvent may absorb water in blood to cloud the present composition.

The composition of the present invention can be prepared by various methods, including conventional high-viscosity type mixing apparatuses.

Such mixing apparatuses can be illustrated by agitators such as a planetary mixer, a roll mill and a homogenizer. These agitators may be equipped with a heating and cooling bath.

In addition to being utilized to separate serum or plasma from blood clot or cell, the composition of the present invention is utilized to separate leukocyte. In this case, several kinds of compositions must be prepared having different viscosities or specific gravities. Different dyes or pigments may be added thereto to distinguish them from each other by the respective colors.

The present invention also includes a blood testing container comprising a separatory container which accommodates the preceding serum or plasma separator composition.

The shape of the separatory container is not particularly specified. The use of a closed-end tubular container 1 shown in FIG. 1 may be preferred, for example. The serum or plasma separator composition 2 is accommodated within the tubular container 1. Blood is first introduced into the tubular container 1. When the container is subsequently centrifuged, the separator composition 2 comes to position between the serum or plasma and solid matter.

The material of the separatory tube is not particularly specified. Examples of materials include thermoplastic resins, e.g., polyethylene, polypropylene, polystyrene, polyethylene terephthalate, polymethyl methacrylate, polyacrylonitrile, polyamide, acrylonitrile-styrene copolymer and ethylene-vinyl alcohol copolymer; thermosetting resins, e.g., unsaturated polyester, epoxy and epoxy-acrylate resins; modified natural resins, e.g., cellulose acetate, cellulose propionate, ethyl cellulose and ethyl chitin; silicate glasses, e.g., soda-lime glass, phosphosilicate glass and borosilicate glass; glasses such as silica glass. The above-listed materials, either in combination thereof or in combination with other secondary materials, can be used. Other materials conventionally known in the art can also be used.

The preceding blood testing container can also be used as a so-called vacuum blood collection tube. In such a case, a closure 3 is attached so as to close an opening of the tubular container 1, as shown in FIG. 1. The closure 3 is constructed in a liquid-tight manner so that blood is prevented from leaking through the closure to outside. Preferably, the closure is air-impermeable to maintain a desired degree of vacuum. The material of such a closure is not particularly specified, and may be at least one type of elastic material selected from natural rubber, synthetic rubber and thermoplastic elastomer. Alternatively, those conventionally known in the art, such as laminated aluminum and aluminum-deposited sheet, may be used.

The blood testing container may further accommodate various additions conventionally known in the art, depending upon the test purposes. Examples of those additions include reagents such as blood coagulants or anticoagulants, glycolysis blockers, deproteinization agents, stabilizers or inhibitors of target components and activators; carriers of the preceding reagents; and supplementary members for assisting intimate mixing of those reagents and blood.

BRIEF DESCRIPTION OF THE DRAWING

FIG. 1 is a longitudinal sectional view which schematically shows one example of a blood testing container in accordance with the present invention.

BEST MODE FOR CARRYING OUT THE PRESENT INVENTION

The below-listed materials were used as formulation ingredients of the composition in the following Examples and Comparative Examples.

1) Cyclopentadiene Based Oligomer oligomer of cyclopentadiene: softening point 103° C., product of Tonex Co., product name: Escorez 251 (ECR 251)

2) Phthalate Ester didecyl phthalate: product of Mitsubishi Gas Chemical Company, Inc., product name: PL200 (flow point −18° C., specific gravity 0.96, viscosity (20° C.) about 0.06 Pa·s)

3) Polycyclic Hydrocarbon Compound partially-hydrogenated triphenyl: product of Nippon Steel Chemical Co., Ltd., product name: ThermS-900 (hydrogenation level about 40%, flow point −10° C. or below, specific gravity 1.01, viscosity (20° C.) about 0.07 Pa·s)

4) Organic Gelling Agent dibenzylidene sorbitol (DBS): product of New Japan Chemical Co., Ltd., product name: Gel All D 5) Silica Fine Particles specific surface area 250 m²/g, product of Tokuyama Corp., product name: Rheolosil DM30S 6) Other Polycyclic Hydrocarbon Compounds dibenzyl toluene: product of Soken Chemical Co., Ltd., product name: NeoSK-OIL 1400 (flow point −30° C. or below, specific gravity 1.04, viscosity (20° C.) about 0.05 Pa·s)

alkyl(bi)phenyl: product of Soken Chemical Co., Ltd., product name: NeoSK-OIL 1300 (flow point −40° C. or below, specific gravity 0.96, viscosity (20° C.) about 0.025 Pa·s)

alkylnaphthalene: product of Nippon Steel Chemical Co., Ltd., product name: ThermS-200S (flow point −10° C. or below, specific gravity 1.00, viscosity (20° C.) about 0.003 Pa·s)

cyclohexylbenzene: product of Aldrich Co., reagent (freezing point 4° C., specific gravity 0.94, viscosity (20° C.) about 0.003 Pa·s)

dicyclohexyl: product of Aldrich Co., reagent (freezing point 4° C., specific gravity 0.86, viscosity (20° C.) about 0.01 Pa·s)

7) Non-polycyclic Hydrocarbon Compound chlorinated paraffin: product of Tosoh Corp., product name: Toyoparax (freezing point −20° C., specific gravity 1.16, viscosity (20° C.) about 2.5 Pa·s)

EXAMPLES 1–12

Preparation of Separator Compositions and Blood Collection Tubes

Didecyl phthalate as a phthalate ester, the polycyclic hydrocarbon compound specified in Table 1, and dibenzylidene sorbitol (DBS) as an organic gelling agent were charged into a 2-liter glass beaker and then heated at 130° C. to bring them into solution. The cycylopentadiene based oligomer was further added and then heated to bring the flask contents into solution. A formulation of each solution is shown in Table 2.

Silica fine particles were added to each solution at 35° C. or below. The resultant was kneaded in a planetary mixer to obtain a separator composition having a specific gravity of 1.04–1.06.

Each separator composition was introduced into 20 hard glass test tubes each having a volume of 10 ml, 1.5 g for each test tube, to prepare blood collection tubes.

(Performance Evaluation)

10 out of 20 blood collection tubes were stored at room temperature for a week. The remaining 10 tubes were stored at 55° C. for a week. After storage, 3 ml of sheep preserved blood containing citric acid was collected in each and every blood collection tube. After 5-minute centrifugation at 1,800 G, the separation condition of plasma from blood cell by the defined separator partition, the presence of hemolysis and the presence of floating oil were visually observed.

Results

The results are shown in Table 4. In Examples 1–12, appearance of floating oil was not observed.

COMPARATIVE EXAMPLES 1–9

Preparation of Separator Compositions and Blood Collection Tubes

The procedure of Examples 1–12 was followed, except that each formulation ingredient was incorporated in the amount specified in Tables 1 and 3, to prepare separator compositions of Comparative Examples 1–9 having specific gravities of 1.03–1.06. In Comparative Example 2, chlorinated paraffin as a non-polycyclic hydrocarbon was used in the place of the polycyclic hydrocarbon.

Each separator composition was introduced into 20 hard glass test tubes each having a volume of 10 ml, 1.5 g for each test tube, to prepare blood collection tubes.

Performance Evaluation

The procedure of Examples was followed, except that centrifugation was performed at 1,800 or 5,000 G, to visually observe the separation condition of plasma from blood cell by the defined separator partition, the presence of hemolysis and the presence of floating oil.

Results

The results are shown in Table 4.

Due probably to the incorporation of excessive organic gelling agent, even a centrifugal force of 5,000 G was not effective to form a partition in Comparative Example 7. The separator composition thus failed to fulfill its function. In Comparative Examples 1–6, 8 and 9, floating oil was observed after either or both of the hot storage and room temperature storage.

TABLE 1

| | Polycyclic Hydrocarbon or Other Compounds | Specific Gravity | Flow or Freezing Point (° C.) | Remarks |
|---|---|---|---|---|
| Ex. 1 | Partially Hydrogenated Triphenyl | 1.007 | <−10 | |
| Ex. 2 | Dibenzyltoluene | 1.04 | <−30 | |
| Ex. 3 | Alkylnaphthalene | 1.002 | <−10 | |
| Ex. 4 | Alkyldiphenyl | 0.96 | <−40 | |
| Ex. 5–12 | Partially Hydrogenated Triphenyl | 1.007 | <−10 | |
| Comp. Ex. 1 | None | 1.16 | | Polycyclic Compound was not Used |
| Comp. Ex. 2 | Chlorinated Paraffin | 0.942 | −20 | Non-Polycyclic Compound |
| Comp. Ex. 3 | Cyclohexylbenzene | 0.864 | 4 | Polycyclic but Having a Freezing Point of Higher than 0° C. |
| Comp. Ex. 4 | Dicyclohexyl | 1.007 | 3.5 | Polycyclic but Having a Freezing Point of Higher than 0° C. |
| Comp. Ex. 5 | Partially Hydrogenated Triphenyl | 1.007 | <−10 | |
| Comp. Ex. 6 | Partially Hydrogenated Triphenyl | 1.007 | <−10 | |
| Comp. Ex. 7 | Partially Hydrogenated Triphenyl | 1.007 | <−10 | |
| Comp. Ex. 8 | Partially Hydrogenated Triphenyl | 1.007 | <−10 | |
| Comp. Ex. 9 | Partially Hydrogenated Triphenyl | 1.007 | <−10 | |

TABLE 2

|  | Cyclopentadiene Based Oligomer ECR251 | Phthalate Ester PL200 | Polycyclic Hydrocarbon Compound Refer to Table 1 | Organic Gelling Agent DBS | Specific Gravity Adjustor DM30S |
|---|---|---|---|---|---|
| Ex. 1 | 100 | 21 | 59 | 0.19 | 5 |
| Ex. 2 | 100 | 21 | 59 | 0.19 | 5 |
| Ex. 3 | 100 | 21 | 59 | 0.19 | 5 |
| Ex. 4 | 100 | 21 | 59 | 0.19 | 7 |
| Ex. 5 | 100 | 30 | 50 | 0.11 | 6 |
| Ex. 6 | 100 | 6 | 77 | 0.34 | 5 |
| Ex. 7 | 100 | 11 | 71 | 0.34 | 5 |
| Ex. 8 | 100 | 21 | 63 | 0.37 | 5 |
| Ex. 9 | 100 | 21 | 60 | 0.15 | 5 |
| Ex. 10 | 100 | 38 | 45 | 0.34 | 5 |
| Ex. 11 | 100 | 7 | 213 | 0.60 | 13 |
| Ex. 12 | 100 | 62 | 21 | 0.34 | 5 |

(Parts by Weight)

TABLE 3

|  | Cyclopentadiene ECR251 | Phthalate Ester PL200 | Other Compounds Refer to Table 1 | Organic Gelling Agent DBS | Specific Gravity Adjustor DM30S |
|---|---|---|---|---|---|
| Comp. Ex. 1 | 100 | 80 | 0 | 0.19 | 5 |
| Comp. Ex. 2 | 100 | 60 | 20 | 0.19 | 5 |
| Comp. Ex. 3 | 100 | 21 | 59 | 0.19 | 5 |
| Comp. Ex. 4 | 100 | 60 | 20 | 0.19 | 8 |
| Comp. Ex. 5 | 100 | 45 | 38 | 0.34 | 5 |
| Comp. Ex. 6 | 100 | 7 | 309 | 0.78 | 19 |
| Comp. Ex. 7 | 100 | 21 | 62 | 5.47 | 1 |
| Comp. Ex. 8 | 100 | 4 | 77 | 0.34 | 5 |
| Comp. Ex. 9 | 100 | 21 | 60 | 0.00 | 5 |

(Parts by Weight)

TABLE 4

|  | Storage Method | Centrifugal Force (G) | Separation Condition | Hemolysis | Oily Matter |
|---|---|---|---|---|---|
| Ex. 1 | Room Temp. | 1800 | ○ | Absent | Absent |
|  | Heated | 1800 | ○ | Absent | Absent |
| Ex. 2 | Room Temp. | 1800 | ○ | Absent | Absent |
|  | Heated | 1800 | ○ | Absent | Absent |
| Ex. 3 | Room Temp. | 1800 | ○ | Absent | Absent |
|  | Heated | 1800 | ○ | Absent | Absent |
| Ex. 4 | Room Temp. | 1800 | ○ | Absent | Absent |
|  | Heated | 1800 | ○ | Absent | Absent |
| Ex. 5 | Room Temp. | 1800 | ○ | Absent | Absent |
|  | Heated | 1800 | ○ | Absent | Absent |
| Ex. 6 | Room Temp. | 1800 | ○ | Absent | Absent |
|  | Heated | 1800 | ○ | Absent | Absent |
| Ex. 7 | Room Temp. | 1800 | ○ | Absent | Absent |
|  | Heated | 1800 | ○ | Absent | Absent |
| Ex. 8 | Room Temp. | 1800 | ○ | Absent | Absent |
|  | Heated | 1800 | ○ | Absent | Absent |
| Ex. 9 | Room Temp. | 1800 | ○ | Absent | Absent |
|  | Heated | 1800 | ○ | Absent | Absent |
| Ex. 10 | Room Temp. | 1800 | ○ | Absent | Absent |
|  | Heated | 1800 | ○ | Absent | Absent |
| Ex. 11 | Room Temp. | 1800 | ○ | Absent | Absent |
|  | Heated | 1800 | ○ | Absent | Absent |
| Ex. 12 | Room Temp. | 1800 | ○ | Absent | Absent |
|  | Heated | 1800 | ○ | Absent | Absent |

TABLE 5

|  | Storage Method | Centrifugal Force (G) | Separation Condition | Hemolysis | Oily Matter |
|---|---|---|---|---|---|
| Comp. Ex. 1 | Room Temp. | 1800 | ○ | Absent | Absent |
|  | Heated | 1800 | ○ | Absent | Present |
| Comp. Ex. 2 | Room Temp. | 1800 | ○ | Absent | Present |
|  | Heated | 1800 | ○ | Absent | Present |
| Comp. Ex. 3 | Room Temp. | 1800 | ○ | Absent | Present |
|  | Heated | 1800 | ○ | Absent | Present |
| Comp. Ex. 4 | Room Temp. | 1800 | ○ | Absent | Present |
|  | Heated | 1800 | ○ | Absent | Present |
| Comp. Ex. 5 | Room Temp. | 1800 | ○ | Absent | Present |
|  | Heated | 1800 | ○ | Absent | Present |
| Comp. Ex. 6 | Room Temp. | 5000 | ○ | Absent | Present |
|  | Heated | 5000 | ○ | Absent | Present |
| Comp. Ex. 7 | Room Temp. | 5000 | X | Absent | N/A |
|  | Heated | 5000 | X | Absent | N/A |
| Comp. Ex. 8 | Room Temp. | 1800 | ○ | Absent | Absent |
|  | Heated | 1800 | ○ | Absent | Present |
| Comp. Ex. 9 | Room Temp. | 1800 | ○ | Absent | Absent |
|  | Heated | 1800 | ○ | Absent | Present |

EFFECTS OF THE INVENTION

Because the serum or plasma separator composition of the present invention includes the polycyclic hydrocarbon compound, compatibility between the cyclopentadiene based oligomer and the phthalate ester is remarkably improved and stabilized.

Also because the polycyclic hydrocarbon compound is nonpolar, the present composition containing this compound causes no adsorption of therapeutic drug in blood and increases the accuracy of monitoring of its concentration.

The use of the composition of the present invention enables provision of a blood testing container which, even when stored either for a long term or under the hot condition, can avoid flotation of oily matter in serum or plasma after centrifugation.

The invention claimed is:

1. A serum or plasma separator composition comprising a polycyclic hydrocarbon compound having an unsaturated and/or saturated cyclic structure in a molecule and a freezing or flow point of 0° C. or below, a cyclopentadiene based oligomer, and a phthalate ester.

2. The serum or plasma separator composition as recited in claim 1, wherein said unsaturated cyclic structure of the polycyclic hydrocarbon compound is an aromatic ring.

3. The serum or plasma separator composition as recited in claim 1, comprising from 1 to 300 parts by weight of the polycyclic hydrocarbon compound having an unsaturated and/or saturated cyclic structure in a molecule and a freezing or flow point of 0° C. or below and from 5 to 40 parts by weight of the phthalate ester, based on 100 parts by weight of the cyclopentadiene based oligomer.

4. A blood testing container having contained therein the serum or plasma separator composition as recited in claim 1.

5. The serum or plasma separator composition as recited in claim 2, containing from 1 to 300 parts by weight of the polycyclic hydrocarbon compound having an unsaturated and/or saturated cyclic structure in a molecule and a freezing or flow point of 0° C. or below and from 5 to 40 parts by weight of the phthalate ester based on 100 parts by weight of the cyclopentadiene based oligomer.

6. A blood testing container having contained therein the serum or plasma separator composition as recited in claim 2.

7. A blood testing container having contained therein the serum or plasma separator composition as recited in claim 3.

* * * * *